(12) United States Patent
Kingsbury

(10) Patent No.: US 11,739,975 B2
(45) Date of Patent: Aug. 29, 2023

(54) VENT COVER

(71) Applicant: Christina H. Kingsbury, Hendersonville, TN (US)

(72) Inventor: Christina H. Kingsbury, Hendersonville, TN (US)

(73) Assignee: Christina H. Kingsbury, Hendersonville, TN (US)

( * ) Notice: Subject to any disclaimer, the term of this patent is extended or adjusted under 35 U.S.C. 154(b) by 0 days.

(21) Appl. No.: 16/162,122

(22) Filed: Oct. 16, 2018

(65) Prior Publication Data
US 2019/0049144 A1    Feb. 14, 2019

Related U.S. Application Data

(63) Continuation-in-part of application No. 29/608,395, filed on Jun. 21, 2017, now Pat. No. Des. 853,551, and a continuation-in-part of application No. 29/608,392, filed on Jun. 21, 2017, now Pat. No. Des. 853,550.

(51) Int. Cl.
| | |
|---|---|
| *F24F 13/08* | (2006.01) |
| *A61L 9/12* | (2006.01) |
| *A61L 9/013* | (2006.01) |

(52) U.S. Cl.
CPC ............ *F24F 13/084* (2013.01); *A61L 9/013* (2013.01); *A61L 9/12* (2013.01); *A61L 9/127* (2013.01); *A61L 2209/16* (2013.01); *A61L 2209/21* (2013.01)

(58) Field of Classification Search
CPC ........ F24F 13/084; F24F 13/082; F24F 13/20; A61L 9/013; A61L 9/12; A61L 9/127

USPC .......................................... 454/275, 367, 291
See application file for complete search history.

(56) References Cited

U.S. PATENT DOCUMENTS

| | | |
|---|---|---|
| D14,132 S | 7/1883 | Drummond |
| 5,240,653 A * | 8/1993 | Ramkissoon ............. A61L 9/12 239/56 |
| D376,006 S | 11/1996 | Smolarski |
| 5,911,632 A * | 6/1999 | Ko ........................... A01C 7/00 47/5.5 |
| D422,061 S | 3/2000 | Lee |
| D462,757 S | 9/2002 | Pettit |
| D510,997 S | 10/2005 | Berger |
| D517,191 S | 3/2006 | Berger |
| D517,192 S | 3/2006 | Berger |
| D522,125 S | 5/2006 | Oosterhuis |
| D528,193 S | 9/2006 | Lee |
| D556,885 S | 12/2007 | Suri et al. |

(Continued)

OTHER PUBLICATIONS

Timesetl (Timesetl 3pcs Stainless Steel Woven Wire 20 Mesh 12"x8"(30x21cm) Metal Mesh Sheet 1mm Hole Great for Air Ventilation—A4. Offered for Sale on Amazon on Apr. 18, 2018).*

(Continued)

*Primary Examiner* — Vivek K Shirsat
(74) *Attorney, Agent, or Firm* — Faegre Drinker Biddle & Reath LLP

(57) ABSTRACT

A self-adhering vent cover allows a user to improve the appearance of a vent while facilitating sufficient airflow for the continued use of a heating, cooling, or air-ventilation system. The present disclosure also provides for the distribution of essential oils within an indoor environment via the use of a heating, cooling, or air-ventilation system.

36 Claims, 10 Drawing Sheets

(56) References Cited

U.S. PATENT DOCUMENTS

| | | | |
|---|---|---|---|
| D596,698 S | 7/2009 | Urriola | |
| D609,327 S | 2/2010 | Mair | |
| D687,524 S | 8/2013 | Heiser | |
| D736,354 S | 8/2015 | Lucas | |
| D738,484 S | 9/2015 | Carroll | |
| D738,485 S | 9/2015 | Carroll | |
| D738,486 S | 9/2015 | Carroll | |
| D762,297 S | 7/2016 | Carroll | |
| D763,431 S | 8/2016 | Carroll | |
| D763,432 S | 8/2016 | Carroll | |
| D774,637 S | 12/2016 | Carroll | |
| D776,249 S | 1/2017 | Carroll | |
| D779,051 S | 2/2017 | Carroll | |
| D796,022 S | 8/2017 | Dechristofaro | |
| D805,628 S | 12/2017 | Green et al. | |
| D853,550 S | 7/2019 | Kingsbury | |
| D853,551 S | 7/2019 | Kingsbury | |
| 2002/0157540 A1* | 10/2002 | Lynn | A45D 20/12 96/222 |
| 2014/0141709 A1* | 5/2014 | Hammer | F24F 13/082 454/284 |

OTHER PUBLICATIONS

Supermagnete (https://web.archive.org/web/20130730062451/https://www.supermagnete.de/eng/faq/ls-this-magnet-isotropic-or-anisotropic., snapshot taken Jul. 30, 2013 recovered through WayBackMachine on Feb. 10, 2021).*

ReVent (https://www.etsy.com/shop/ReVentDesigns?ref=simple-shop-header-name&listing_id=636269367).*

"Magically Magnetic"-Black or White Magnetic Vent Cover. Nov. 22, 2012 (Year: 2012).*

Magically_Magnetic-Date (Year: 2012).*

Beauti-Vent, The Original Magnetic Vent Cover for Return Vents, Etsy, https://www.etsy.com/listing/633668956/beauti-vent-the-original-magnetic-vent?gpla=1&gao=1&&utm_source=google&utm_medium=cpc&utm_campaign=shopping_us_b-home_andJiving-home_decor-walLdecor-other&utm Listed Nov. 4, 2018, Visited Online Nov. 18, 2018.

Iron Age Designs Interlaken Home Register Cover, Amazon, https://www.amazon.com/dp/B00BH3IGOG/ref=sxbs_sxwds-stppvp_1 ?pf_rd Date First Available Feb. 13, 2013, [Visited Online Nov. 18, 2018].

Jenia Aromatherapy Diffuser Vent Clip—Car Air Freshener Fragrance—Stainless Steel Essential Oil Locket—Calm Driving, Amazon, Date First Available Feb. 22, 2016, retrieved on Sep. 28, 2018, 9 pages.

Omni ReVent Cover—Decorative Vent Covers, Etsy, https://www.etsy.com/in-en/listing/579986805/omni-revent-cover-decorative-vent-covers, listed on 2018, visited on Jun. 26, 2020, 14 pages.

ReVent Covers, Facebook page, available online at < https://www.facebook.com/reventcovers/>, established Jun. 12, 2018, 4 pages.

ReVent Covers-Decorative Magnetic Wall Vent Covers, Etsy, https://www.etsy.com/listing/613514207/revent-covers-decorative-magnetic-wall?ref=shop_home_active_6&frs=1 Listed Sep. 3, 2018, [Visited Online Nov. 18, 2018].

SteelCrest Intelligent Design, Omni Register Cover, https://www.steelcrestonline.com/portfolio/omni/ Copyright 2015, [Visited Online Nov. 18, 2018].

SteelCrest Intelligent Design, Santa Fe Register Cover, https://www.steelcrestonline.com/portfolio/santa-fe/ Copyright 2015, [Visited Online Nov. 18, 2018].

Vent Covers Unlimited, established Apr. 1, 2013, available online at < https://ventcoversunlimited.com/ >, retrieved on Jun. 26, 2020, 6 pages.

* cited by examiner

VENT COVER

CROSS-REFERENCE TO RELATED APPLICATION

This application claims priority to U.S. Design application Ser. No. 29/608,392 filed Jun. 21, 2017, the entire disclosure of which is hereby expressly incorporated by reference herein. This application additionally claims priority to U.S. Design application Ser. No. 29/608,395 filed Jun. 21, 2017, the entire disclosure of which is hereby expressly incorporated by reference herein.

BACKGROUND OF THE DISCLOSURE

1. Field of the Disclosure

The present invention relates generally to a vent cover for improving the appearance of a heating, cooling, or air-ventilating system vent while facilitating appropriate airflow through the vent and, more particularly, to a vent cover for use with an existing vent which can be easily secured to the vent without the use of tools.

2. Description of the Related Art

Heating, ventilating, and air conditioning systems keep indoor environments comfortable and healthy. To allow these systems to function, ductwork is installed throughout a building to allow air to cycle to and from these systems. Vents are connected to terminal ends of ducts as the ducts terminate in rooms of a building. For the systems to run efficiently, the air within the ductwork ideally remains balanced, which requires the amount of air entering the ducts from return vents to generally match the air exiting the ducts through supply vents. As a result, buildings are equipped with several return and supply vents throughout, each of which incorporate a vent to direct air flow in to return air or out of (e.g. conditioned air) the heating, ventilating and air conditioning system.

At times, these vents are found to be unsightly or located in inconvenient places, and as a result they are covered with furniture, art, or the like to mask the appearance of the vent. Alternately, replacement ornate vents are available to provide an ornate appearance that may be more attractive to a building's occupant. However, these solutions may impede the performance of the heating, cooling, and air ventilation systems, are economically inefficient, and are difficult and time consuming for a homeowner or building manager to implement.

Additionally, with the discovery of the benefits of essential oils, consumers desire to find new and better ways to add the benefits of smell therapy or essential oil inhalation to their environments. Integrating the use of essential oils into ventilation systems may boost a user's mental health, respiratory system, immune system, sleep health, and focus, along with other benefits. Integration of essential oils in the home is therefore desired.

SUMMARY OF THE DISCLOSURE

The present disclosure provides a self-adhering vent cover that allows a user to improve the appearance of an existing vent while facilitating sufficient airflow for the continued use of a heating, cooling, or air-ventilation system. The present disclosure also provides for the distribution of essential oils within an indoor environment in conjunction with a heating, cooling, or air-ventilation system.

In an embodiment, the disclosure provides a vent cover comprising a pliable lamella with an exposed side and a vent side, the pliable lamella having an outer perimeter. The vent cover of this embodiment further comprises a fastener presented from the vent side of the pliable lamella, the fastener configured to removably fasten the pliable lamella to the vent, with the vent side of the lamella facing the vent. The vent cover of this embodiment also comprises an ornamental pattern cut into the pliable lamella which defines a plurality of openings to allow airflow through the pliable lamella. The plurality of openings account for a majority of an area defined by the outer perimeter of the pliable lamella.

In an alternate embodiment, the disclosure provides a heating, ventilating, and air-conditioning system comprising an air handler and a vent comprising a plurality of airflow apertures in fluid communication with the air handler. The system of this embodiment also comprises a vent cover configured to removably couple to the vent, the vent comprising a pliable lamella with an exposed side, a vent side, and an outer perimeter, as well as a fastener presented from the vent side of the pliable lamella to removably fasten the pliable lamella to the vent with the vent side of the lamella facing the vent, and an ornamental pattern cut into the pliable lamella. The ornamental pattern defines a plurality of openings to allow airflow from the vent through the pliable lamella, and the plurality of openings account for a majority of an area defined by the outer perimeter of the pliable lamella. In alternative terms of the present disclosure, the system further comprises a diffuser comprising a cellular material capable of receiving evaporative liquid and a cover coupled to the cellular material, wherein the diffuser is configured to removably couple to the vent cover.

In yet another embodiment, the disclosure provides a method of distributing an airflow from an air handler. The method comprises the step of locating a vent in fluid communication with the air handler, where the vent comprises a plurality of airflow apertures for directing the airflow and a vent exterior surface transverse to the airflow. The method also comprises the step of covering the vent with a pliable lamella having an exposed side and a vent side, including the step of facing the vent side toward the vent exterior surface. The method further comprises securing the pliable lamella to the vent so that the pliable lamella presents an ornamental pattern defining a plurality of openings to allow airflow through the pliable lamella.

Additional features and advantages of the present invention will become apparent to those skilled in the art upon consideration of the following detailed description of the illustrative embodiment exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
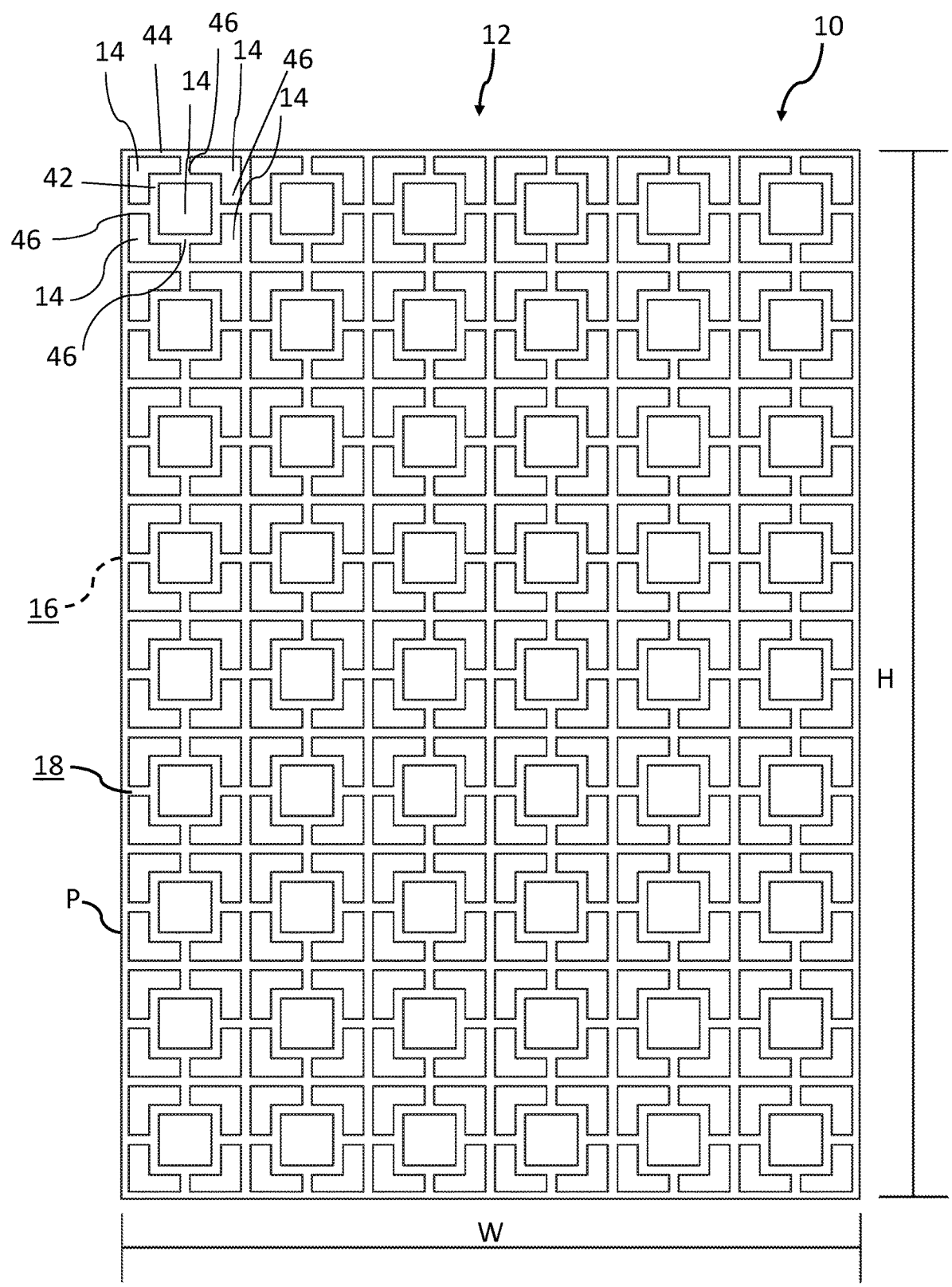
FIG. 1 is a plan view of a vent cover for aesthetically improving an existing vent of a heating, ventilation, and air-conditioning system.

For the purposes of promoting an understanding of the principles of the present disclosure, reference will now be made to the embodiments illustrated in the drawings, which are described herein. The embodiments disclosed herein are not intended to be exhaustive or to limit the invention to the precise form disclosed. Rather, the embodiments are chosen and described so that others skilled in the art may utilize their teachings. Therefore, no limitation of the scope of the claimed invention is thereby intended. The present invention includes any alterations and further modifications of the illustrated devices and described methods and further applications of principles in the invention which would normally occur to one skilled in the art to which the invention relates.

Figure 2:
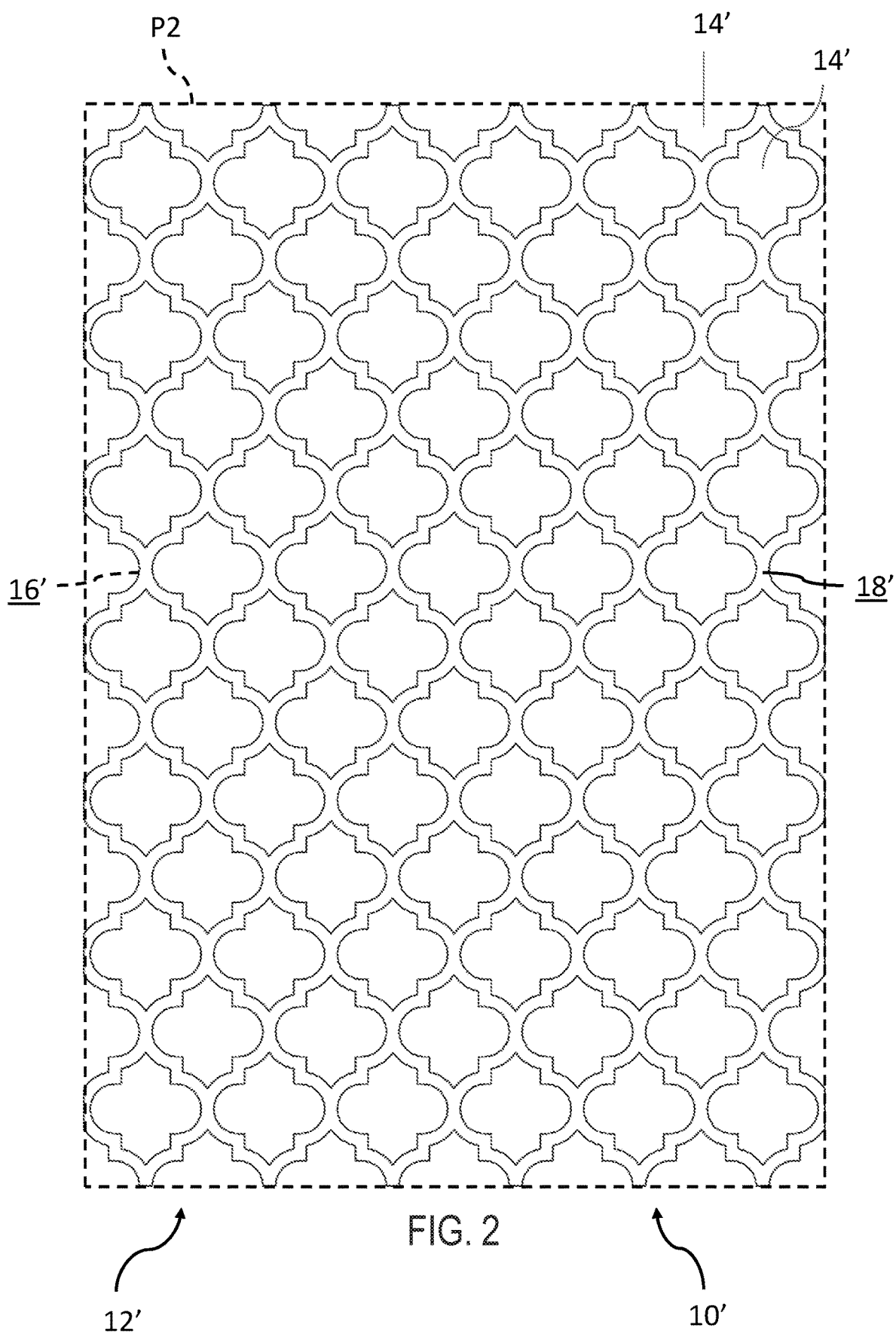
FIG. 2 is a plan view of another vent cover for aesthetically improving an existing vent of a heating, ventilation, and air-conditioning system.

Referring initially to FIG. 1, vent cover 10 is shown. Vent cover 10 comprises a thin sheet of material, e.g., less than 1 mm, such as approximately 0.8 mm, intended to create an ornamental layer of decoration over the vent of a heating, ventilating, or air conditioning system to increase the aesthetic value of the vent. Ornamental pattern 12, as illustrated by FIG. 1, comprises a repeating pattern of an inner square 42 defining an internal aperture 14 surrounded by an outer square 44, with connectors 46 connecting inner square 42 and outer square 44 and defining apertures 14 therebetween. This pattern is marked with reference numerals only in the upper right hand corner of FIG. 1, but repeats in a 6×9 grid to complete vent cover 10. As illustrated by FIG. 2, alternate ornamental pattern 12' may be used for vent cover 10'. Other ornamental patterns may be utilized. Typically, an ornamental pattern will offer a symmetrical, repeating geometric design as in the two exemplifications depicted herein. While several alternative vent covers (10, 10', and 110) are described herein, descriptions of each generally extend to the others, unless specifically noted.

Still referring to FIGS. 1 and 2, openings 14 and 14' of patterns 12 and 12' account for a majority of patterns 12 and 12'. For example, taking the total area defined by the perimeter "P" or "P2" of vent covers 10 or 10' (i.e., the width "W" multiplied by the height "H" of vent cover 10 or 10') and comparing the total area of all of openings 14 or 14', respectively, taken in a central plane through vent cover 10 or 10', the total area of all of openings 14 or 14' accounts for greater than 50% of the total area defined by the perimeter P" or "P2" so that airflow from an operating air handler 15 (FIG. 7) of the heating, ventilating, and air conditioning system is not substantially affected when exiting apertures of a covered vent. Perimeter "P" or "P2" may be a physical extent of cover 10 as shown in FIG. 1 or may be defined by a phantom line intersecting the outer extents of vent cover 10 or 10' as shown in FIG. 2. As demonstrated by FIG. 1, openings 14 may be used to create pattern 12 by repeating the pattern of openings separated by solid material. Specifically, in exemplary embodiments, openings 14 and 14' account for approximately 55%, 65%, 75%, 85%, or 95% of patterns 12 and 12' cut into vent covers 10 and 10'. In exemplary embodiments, vent cover 10, 10', 110 does not affect airflow through the existing vent 24 at all, while in alternate embodiments airflow through the existing vent 24 may be affected by the application of vent cover 10, 10', 110 only in slight amounts, for example, by a decreased airflow of 10% or less as compared to a completely unobstructed vent 24.

Referring to FIG. 1, vent cover 10 is comprised of a pliable lamella that allows vent cover 10 to easily be stored, packaged, and formed to complement a vent cover. For example, vent cover 10 may be rolled from one end to the other around an axis parallel to height "H" or vent cover 10 may be rolled from one end to the other around an axis parallel to width "W." When rolled, vent cover 10 forms a cylinder with a diameter of approximately two to four inches. In one exemplary embodiment, the diameter of the rolled cylinder is approximately 3.4 inches. When unrolled, vent cover 10 presents initial height "H" of approximately 31 to 33 inches and initial width "W" of 21 to 23 inches. In one exemplary embodiment, vent cover 10 presents initial height "H" of approximately 32.25 inches and initial width "W" of 21.5 inches. When unrolled, vent cover 10 also presents a thickness of approximately one millimeter or less. In one exemplary embodiment, vent cover 10 presents a thickness of approximately 0.89 millimeters. In other embodiments, alternate dimensions may be presented.

In an exemplary embodiment, vent cover 10 is comprised of an isotropic magnet sheet, such as a rubber magnet sheet. On first side 16 of vent cover 10, the sheet is magnetized for attachment to a vent comprising a ferrous material or any other material that may be capable of being attracted by a magnet. On second side 18 of vent cover 10, a polymer may be colored, laminated to cover 10, and used for exposed ornamentation. Specifically, in an exemplary embodiment, vent cover 10 is produced with an isotropic magnet sheet with first side 16 magnetized and MUV coated, and second side 18 laminated with color PVC. In alternate embodiments, other pliable materials may be used to produce vent cover 10. Any commercially available PVC coated magnetic sheet could be utilized, with one or both sides presenting magnetic properties.

One suitable commercially available magnetic sheeting is ZIP GRIP Flexible Magnetic Sheeting available from Master Magnetics, Inc. headquartered in Castle Rock, Colo. Particularly, ZIP GRIP Flexible Magnetic Sheeting is made by combining a dry mixture of ferrite powder and rubber polymer resin. The dry mixture is mixed, calendered and ground; then formed by rollers into magnetic sheeting. The formed material is then magnetized, laminated with vinyl or adhesive, cut to size, and rolled for shipment.

Figure 3:
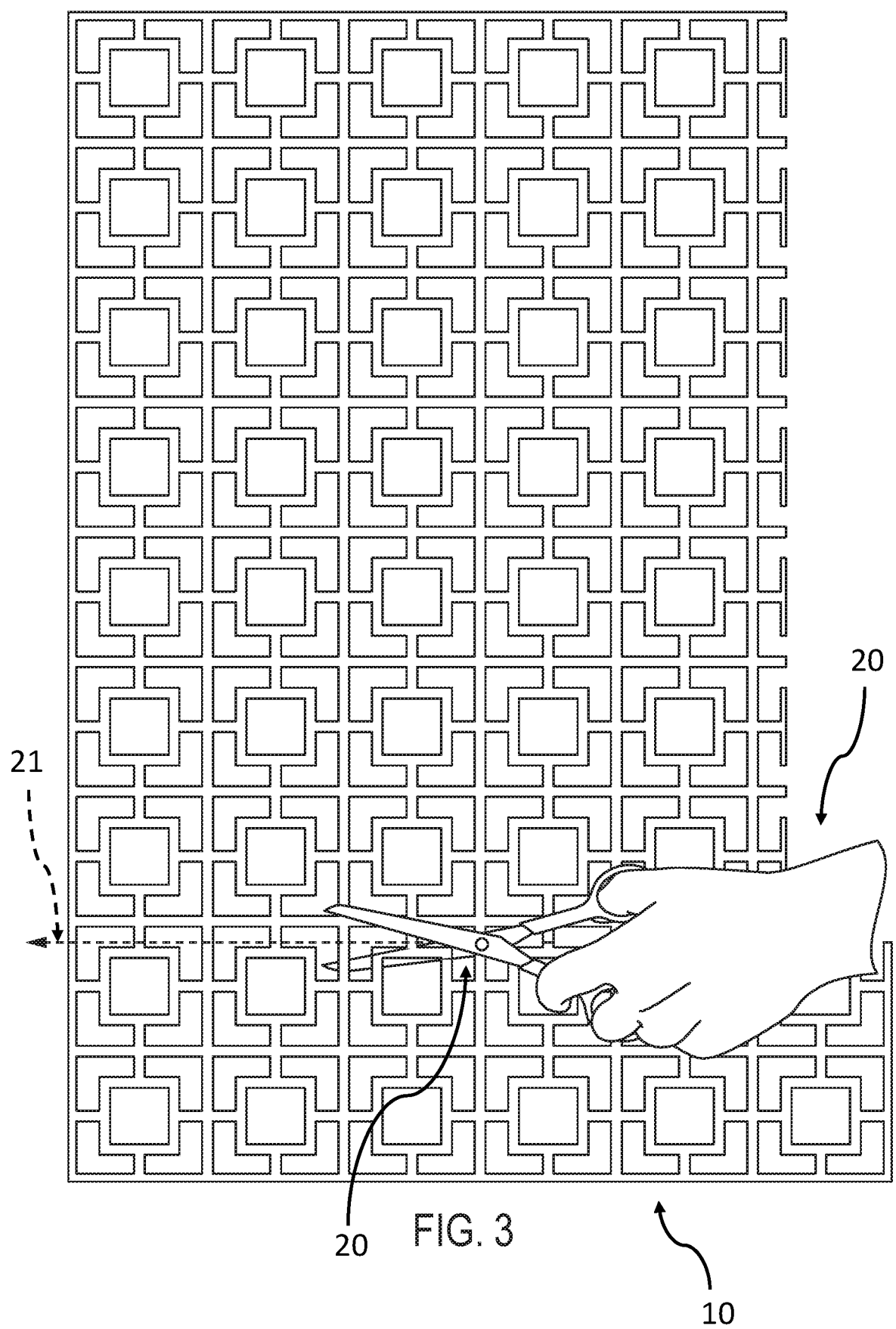
FIG. 3 is a plan view of the vent cover of FIG. 1, illustrating a user cutting the vent cover of FIG. 1 so that the vent cover is sized to complement an existing vent.
Figure 4:
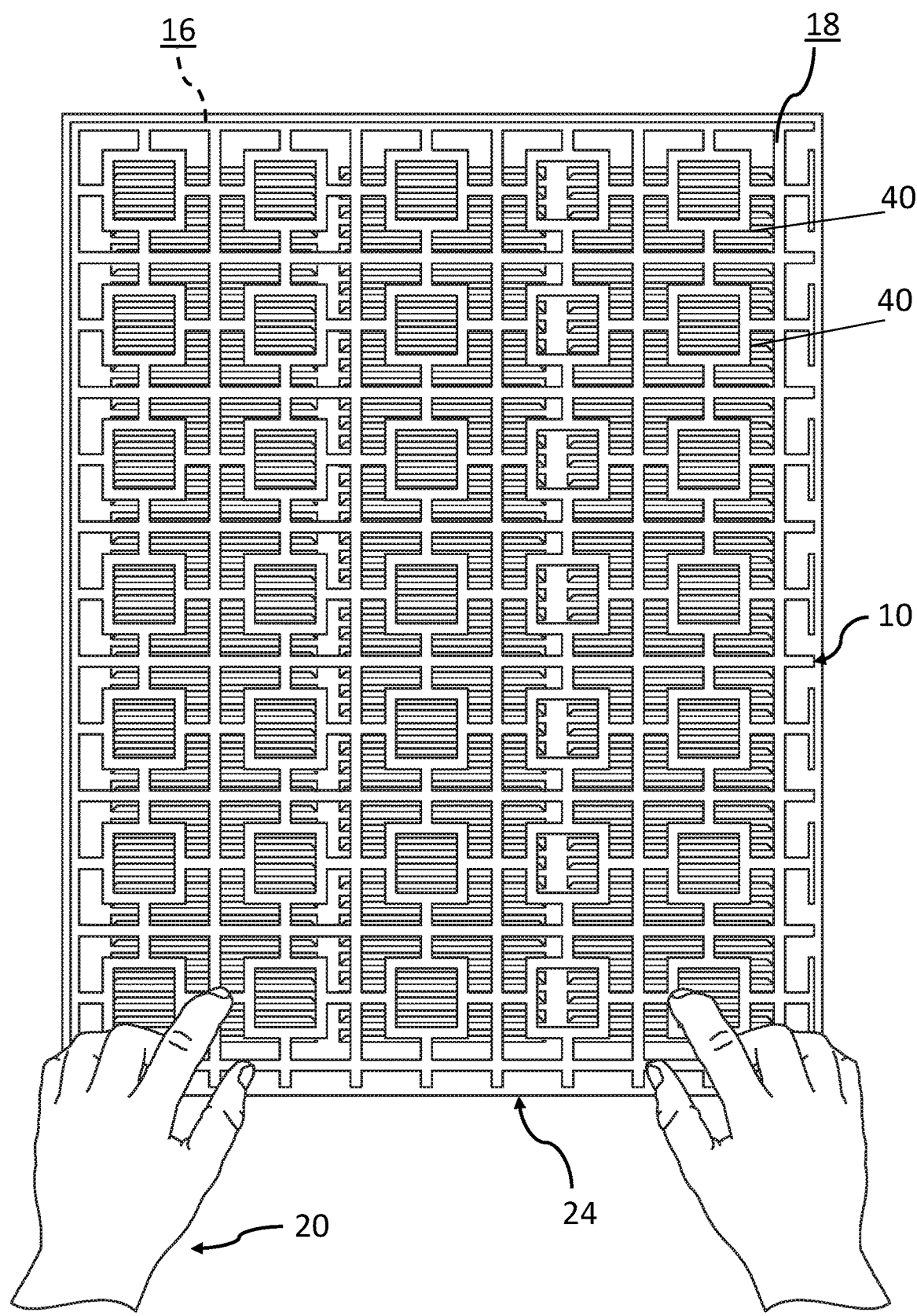
FIG. 4 is an illustration of a user placing the vent cover of FIG. 1 over an existing vent so that the vent cover is adhered to the vent by magnetic force.

As illustrated by FIG. 3, vent cover 10 may be modified to complement alternately sized vents. For example, heating, ventilating, and air conditioning systems may utilize air return vents and air distribution vents of varying sizes. In an embodiment, user 20 is able to cut vent cover 10 along line 21 using scissors 22 so that vent cover 10 complements a targeted vent. Line 21 may be placed in any shape and in any location on vent cover 10 that user 20 desires. User 20 may also use alternate tools to cut vent cover 10, including but not limited to a knife, a razor, a pair of shears, a box cutter, etc. Vent cover 10 may be cut to provide the user with an overall pleasing combination of vent cover 10 and the vent. For example, to complement a vent, vent cover 10 may be cut to an outer perimeter shape congruent with the outer perimeter shape of the vent. Vent cover 10 may be cut to the same size as the vent or a size larger or smaller than the vent. For example, vent cover 10 may be cut to a size 105% of the size of the vent. Alternately, vent cover 10 may be cut to a size smaller than the vent, such as 98% of the size of the vent or smaller (FIG. 4). FIG. 4 illustrates vent cover 10 complementing vent 24 by being positioned centrally within the perimeter of vent 24.

Such scaling of vent cover 10 may retain the outer shape of the existing vent, while covering more or less total area than the vent. In alternative embodiments, sizing is effected in a way that preserves a symmetrical pattern of vent cover 10. With the existing vent positioned centrally within the symmetrical pattern of vent cover 10, vent cover 10 can be said to complement the existing vent. Similarly, with a vent cover 10 that is congruent or substantially congruent (i.e., has the same shape, but is scaled up or down) to the existing vent and positioned centrally within (scaled down), around (scaled up) or over (congruent) the existing vent, vent cover 10 can be said to complement the existing vent.

As illustrated by FIG. 4, vent cover 10 may be adhered to vent 24 of a heating, ventilating, and air conditioning system by magnetic attraction. Specifically, in an embodiment, first side 16 of vent cover 10 comprises magnetized material (the opposite side may be magnetized also), including anything capable of generating a magnetic field. When applied to vent 24 comprised of ferrous material or anything else that is capable of being attracted by a magnet, magnetized first side 16 couples to vent 24 to hold vent cover 10 in place. Vent 24 includes airflow apertures 40, only some of which are numbered in the figures. Throughout the figures, in an effort to simplify the figures and make them more readable, repeated structures/elements are not all numbered. Airflow apertures 40 can take the form of louvered slots sized and shaped to direct airflow through vent 24.

Figure 5:
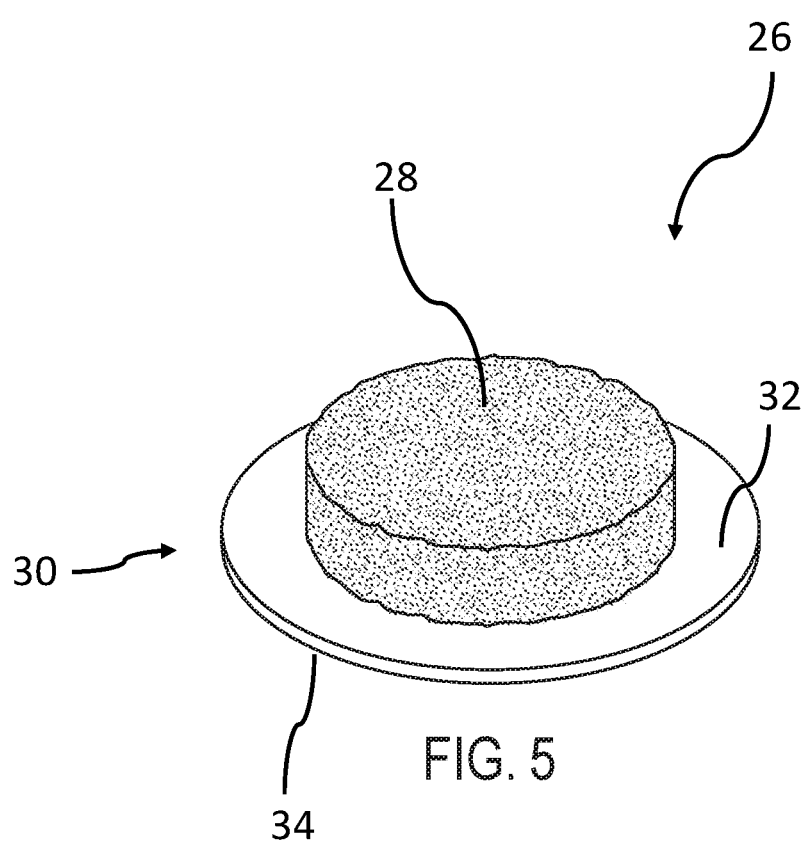
FIG. 5 is a perspective view of a diffuser to be used in conjunction with a vent cover for aesthetically improving an existing vent of a heating, ventilation, and air-conditioning system.
Figure 6:
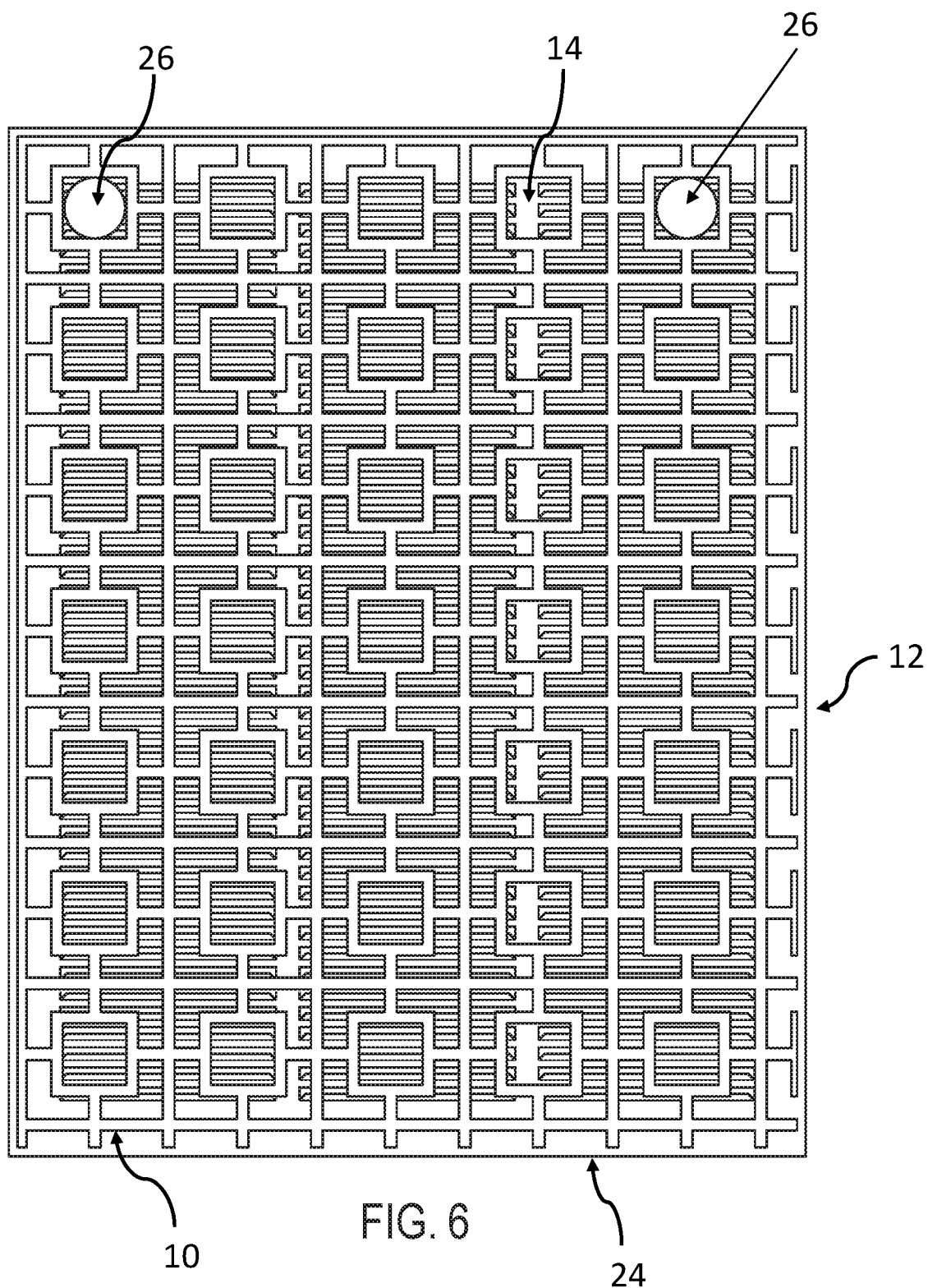
FIG. 6 is an illustration of a pair of the diffusers of FIG. 5 being used in conjunction with the vent cover of FIG. 1.
Figure 7:
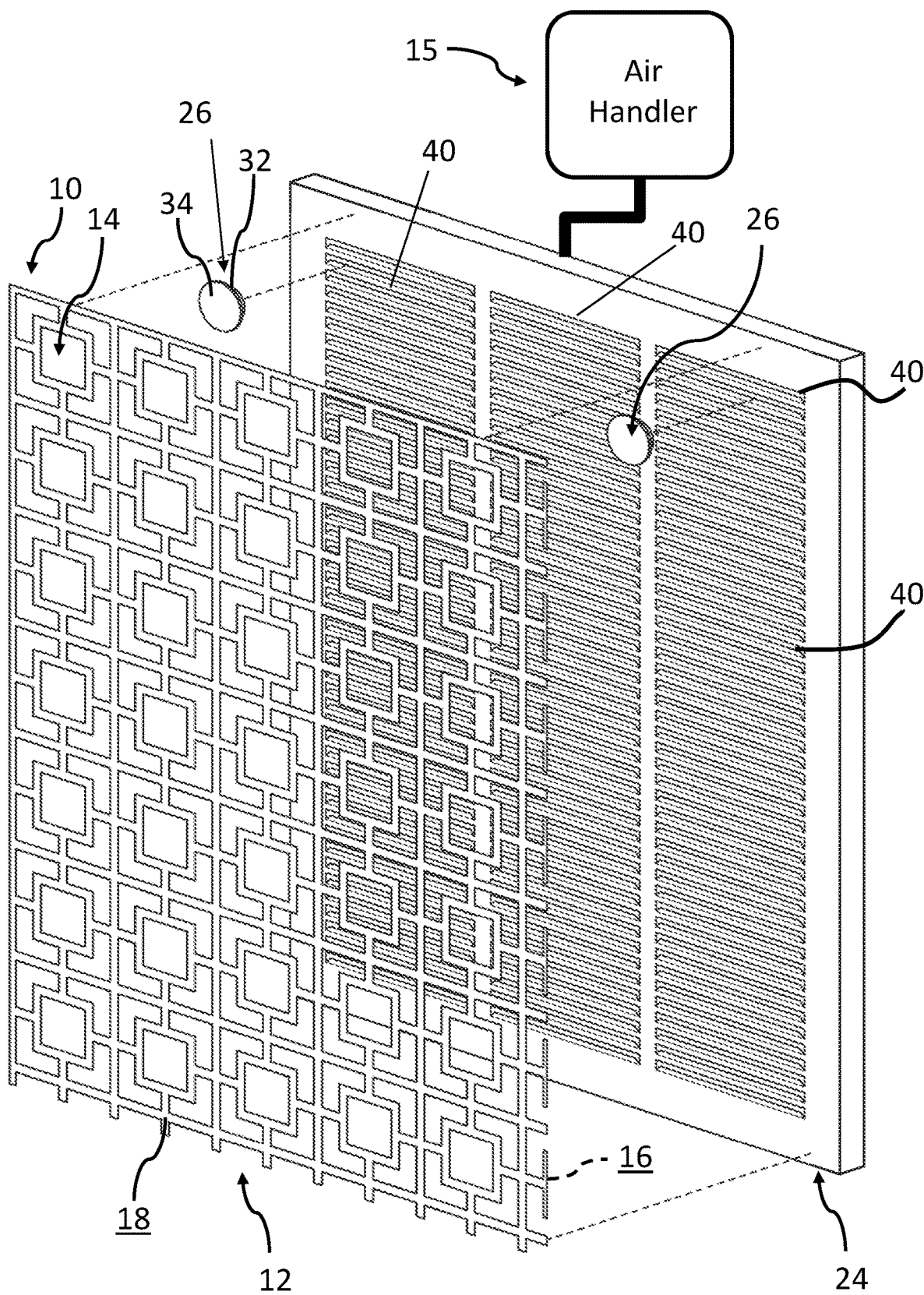
FIG. 7 is an exploded view of the diffuser and the vent cover of FIG. 6.
Figure 8:
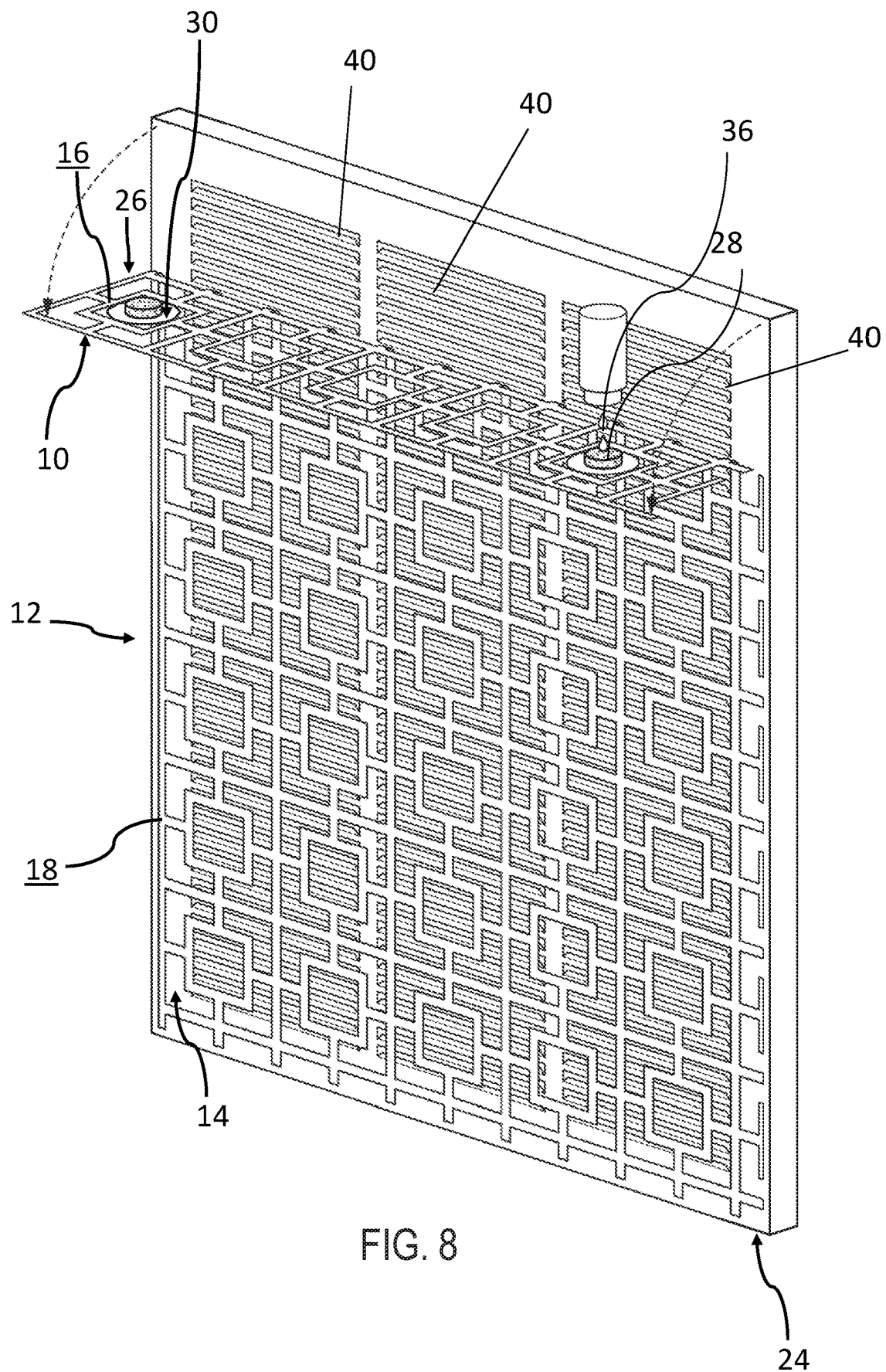
FIG. 8 is an illustration of adding an evaporative liquid to the diffuser of FIG. 5 while the diffuser is being used in conjunction with the vent cover of FIG. 1.

Referring to FIGS. 5-8, a diffuser 26 may be used in conjunction with vent cover 10 as a method of introducing essential oils or other evaporative liquids, such as fragrances into the air distributed by the air handler (FIG. 7). As shown by FIG. 5, diffuser 26 comprises cellular material 28 and cover 30. Cellular material 28 is porous so that evaporative liquids may be added to and held by cellular material 28 for later evaporation. Cellular material 28 may be comprised of nylon, polyester, polymer, wool, or other materials. Additional exemplary materials useable as cellular material 28 are: felt, cotton fiber, wood chipboard (with sheets laminated one on another to the desired thickness), or cork. In the exemplification illustrated, cover 30 extends radially beyond the perimeter of cellular material 28. In alternative configurations, cover 30 will be positioned within the perimeter of cellular material, with cellular material 28 extending beyond the perimeter of cover 30.

Similar to vent cover 10, in an exemplary embodiment, cover 30 is comprised of an isotropic magnet sheet, which is coupled to cellular material 28. For example, cellular material 28 may be glued or otherwise adhered to cover 30. On a first side 32 of cover 30, the sheet may be magnetized to removably couple to vent cover 10 (FIG. 1) or any other material that may be capable of being attracted by a magnet. On a second side 34 of cover 30, a polymer may be colored, laminated, and used for exposed ornamentation. In alternate embodiments, second side 34 may be magnetized to removably, magnetically couple to vent cover 10 (FIG. 1) or directly to vent 24. Specifically, in an exemplary embodiment, cover 30 is produced with an isotropic magnet sheet with first side 32 magnetized and MUV coated, and second side 34 laminated with color PVC. In an alternate exemplary embodiment, cover 30 is produced with an isotropic magnet sheet with second side 34 magnetized and MUV coated. In other embodiments, other materials may be used to produce cover 30, including plastics or other polymers, wood, fabric, etc., and may have magnetic material embedded therein. Any commercially available PVC coated magnetic sheet may be utilized to form cover 30, with one or both sides presenting magnetic properties.

Referring to FIGS. 6 and 7, diffuser 26 may be used in conjunction with vent cover 10 to create an aesthetic pattern over existing vent 24. When diffuser 26 is used in conjunction with vent cover 10, diffuser 26 becomes part of the aesthetic pattern and may in some embodiments be camouflaged within the design of vent cover 10. For example, a plurality of diffusers 26 may be placed in each of four corners of vent cover 10. Alternately, a plurality of diffusers could be incorporated with vent cover 10 to create a repeating pattern. Repeating and/or symmetrical patterns may be used to camouflage diffusers 26 with vent cover 10. As shown in FIGS. 6 and 7, a plurality of diffusers 26 may be used. In other embodiments, only one diffuser 26 may be utilized. Diffuser 26 may be placed anywhere within the pattern 12 that the user chooses. While diffuser 26 may be placed near the top of vent cover 10 as shown in FIGS. 6 and 7, diffuser 26 may also be placed in a variety of other locations within the pattern 12 of vent cover 10. Diffuser 26 is coupled to vent cover 10 in a variety of ways, as described herein, to facilitate airflow in to or out of vent 24 encountering diffuser 26 and facilitating evaporation of the essential oil or other evaporative liquid contained therein. When used in this document, "coupled" does not necessarily denote the joining of only two elements or the direct joining of elements. For example, two elements may be "coupled" by an intervening third element.

In an exemplary embodiment diffuser 26 is configured to be interposed between vent 24 of a heating, ventilating, and air-conditioning system and vent cover 10 through magnetic attraction. Vent cover 10 may assist in holding diffuser 26 in place through the use of magnetic attraction by inserting diffuser 26 between the magnetized first side 16 of vent cover 10 and existing vent 24. When vent cover 10 is used to assist is holding diffuser 26 in place, diffuser 26 is sized, shaped, or otherwise designed so that it will not pass through the openings 14 of vent cover 10, so that diffuser 26 may be interposed between vent cover 10 and vent 24 and held in place by the adherence of vent cover 10 to vent 24. In an alternate embodiment, cellular material 28 of diffuser 26 may be sized so that diffuser 26 may couple directly to existing vent 24 through magnetic attraction. Specifically, cellular material 28 will sit proud of cover 30 a distance that will allow cover 30 to magnetically adhere to vent 24, with cellular material 28 positioned between cover 30 and vent 24. In such an alternate embodiment, diffuser 26 may couple at any point on existing vent 24 without having direct contact with vent cover 10. In further alternative embodiments, diffuser 26 may be directly adhered to vent 24 without also utilizing a vent cover 10, 10', or 110 in connection with the vent 24 to which diffuser is adhered to by magnetism. Cover 30 may exhibit magnetic properties on its side facing cellular material 28 (first side 32) such that diffuser 26 may be magnetically adhered to vent 24 with cellular material 28 positioned between cover 30 and vent 24. Cover 30 may also (or instead) exhibit magnetic properties on its side facing away from cellular material 28 (second side 34) such that diffuser 26 may be magnetically adhered to vent 24 with cellular material 28 protruding outwardly from vent 24 and with cover 30 sandwiched between cellular material 28 and vent 24.

Referring to FIG. 7, evaporative liquid 36 may be added to diffuser 26 by removing all of or a portion of vent cover 10 and diffuser 26 from vent 24 and adding the evaporative liquid to cellular material 28 for later evaporation. When diffuser 26 is in place (FIG. 6) and air handler 15 of the heating, ventilating, and air-conditioning system is operable, the movement of air over cellular material 28 of diffuser 26 facilitates the evaporation of evaporative liquid 36 into the building serviced by vent 24. The cells or pores of cellular material 28 are sized to cooperate with chosen essential oils to hold sufficient amounts of essential oil for an evaporative duration. Cellular material 28 may also be incorporated directly into a vent cover of the present disclosure. More particularly, cellular material 28 may be adhered (without cover 30) to the vent side of a vent cover or may simply be sandwiched between the vent cover and the underlying vent.

Figure 9:
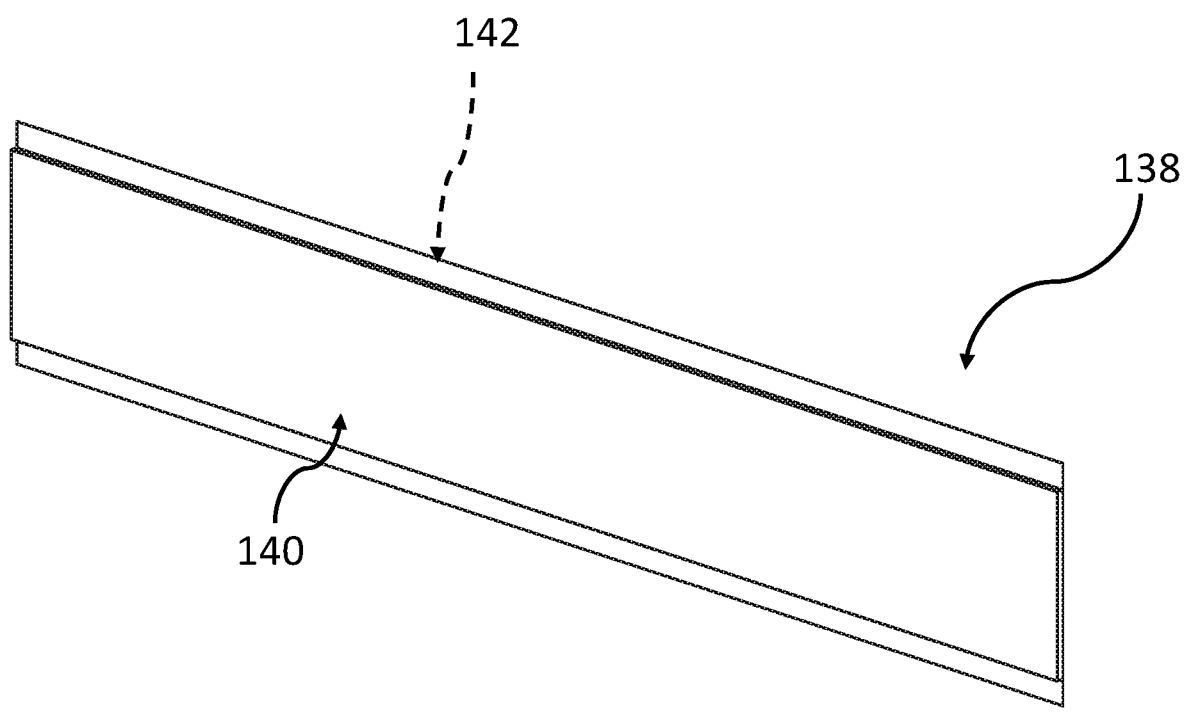
FIG. 9 is a perspective view of a double-sided adhesive strip.
Figure 10:
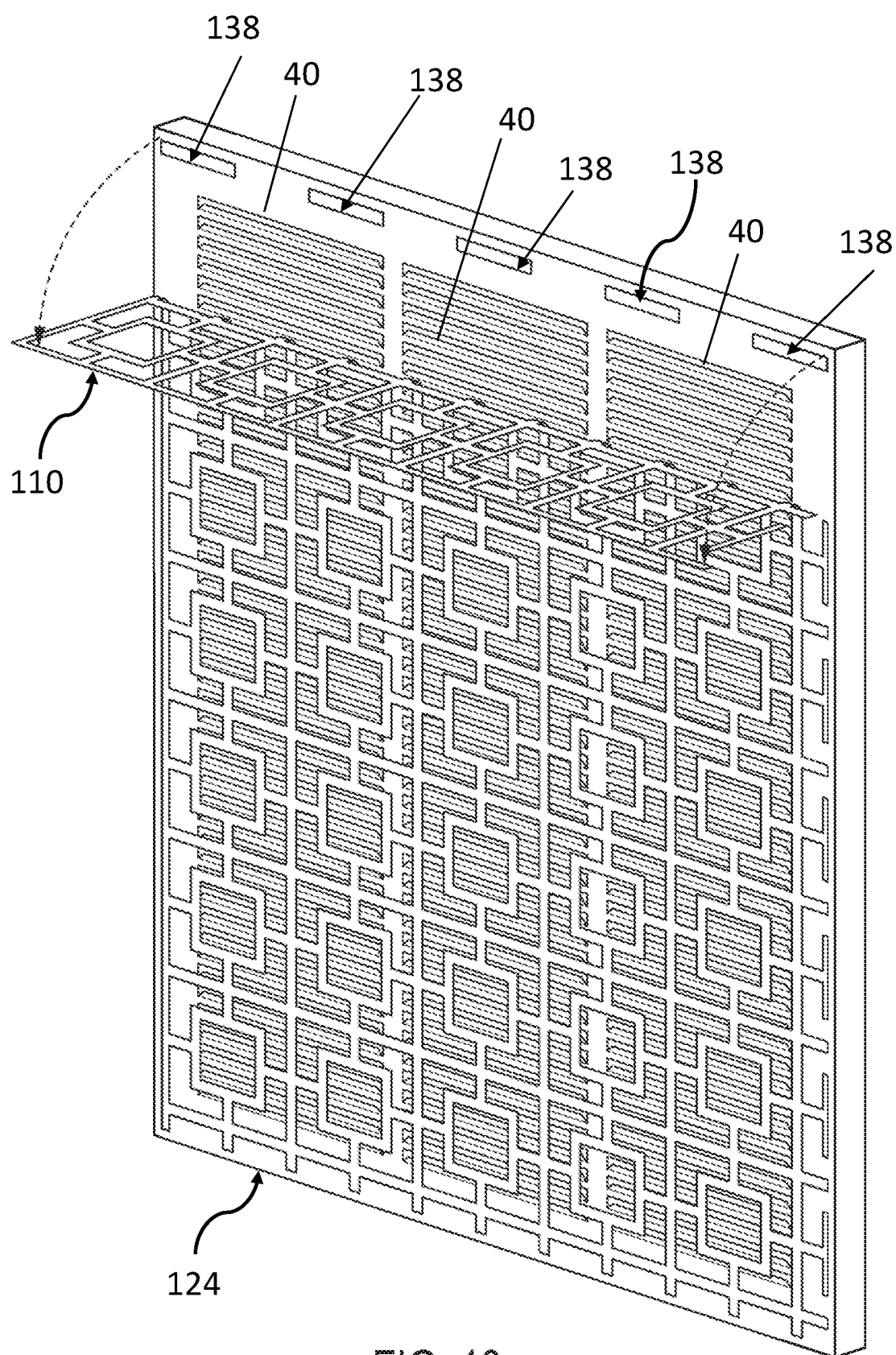
FIG. 10 is an illustration of the adhesive strip of FIG. 9 being used in conjunction with the vent cover of FIG. 1 to adhere the vent cover to an existing vent.

Referring to FIGS. 9 and 10, in an alternate embodiment, existing vent 124 of a heating, ventilating, and air-conditioning system is not comprised of ferrous material or other material capable of attracting a magnet. Alternately, vent cover 110 is not comprised of a magnetic material. In such a situation, vent cover 110 may be adhered to vent 124 using adhesive 138. As shown in FIG. 9, adhesive 138 is a double-sided adhesive that is initially presented with adhesive covers 140, 142.

Now referring to FIG. 10, vent cover 110 may be adhered to vent 124 by first removing first adhesive cover 142 and pressing the uncovered side of adhesive 138 to vent 124 so that adhesive 138 is securely coupled to vent 124. Then, adhesive cover 140 is removed and vent cover 110 is pressed against the uncovered side of adhesive 138. Multiple adhesive strips may be used during this process to ensure that vent cover 110 is securely adhered to vent 124. Alternatively, after first removing first adhesive cover 142, the uncovered side of adhesive 138 may be adhered to vent cover 110, with adhesive cover 140 subsequently being removed to expose the underlying adhesive which may then be adhered to vent 124.

With the adhesion of the vent covers (10, 10', 110) of the present disclosure to an existing vent being accomplished without tools (i.e., toolless adhesion), the appearance of an existing vent screwed or bolted in place at the end of a duct can be improved without requiring removal and replacement of the existing vent.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A vent cover for covering a vent, comprising:
a pliable lamella with an exposed side and a vent side, the pliable lamella having an outer perimeter;
a lamella fastener presented from the vent side of the pliable lamella, the lamella fastener configured to removably fasten the pliable lamella to the vent with the vent side of the lamella facing the vent; and
a pattern cut into the pliable lamella, the pattern defining a plurality of openings to allow airflow through the pliable lamella, wherein the plurality of openings account for a majority of an area defined by the outer perimeter of the pliable lamella.

2. The vent cover of claim 1, wherein the lamella fastener comprises a magnet.

3. The vent cover of claim 1, wherein the lamella fastener comprises a double-sided adhesive with a first side of the double-sided adhesive adhered to the vent side of the pliable lamella and a second side of the double-sided adhesive facing outwardly from the vent side of the pliable lamella for adhesion to the vent.

4. The vent cover of claim 1, in combination with the vent.

5. The vent cover of claim 1, the vent cover further comprising a diffuser, comprising: a cellular material capable of receiving evaporative liquid.

6. The diffuser of claim 5, wherein the diffuser further comprises a cover covering the cellular material, the cover extending beyond a perimeter of the cellular material.

7. The diffuser of claim 6, the cover further comprising a diffuser fastener configured to removably fasten to the pliable lamella.

8. The diffuser of claim 7, wherein the diffuser fastener of the cover of the diffuser comprises a magnet.

9. The diffuser of claim 5, wherein the diffuser defines a surface area having a size and geometry that will not pass thorough the plurality of openings.

10. The vent cover of claim 1, wherein the plurality of openings account for at least 75% of the area defined by the outer perimeter of the pliable lamella.

11. A heating, ventilating, and air-conditioning system, comprising:
a vent comprising a plurality of airflow apertures;
a vent cover removably coupled to the vent, the vent cover comprising:
a pliable lamella with an exposed side and a vent side, the pliable lamella having an outer perimeter;
a fastener presented from the vent side of the pliable lamella, the fastener removably fastening the pliable lamella to the vent with the vent side of the lamella facing the vent; and
a pattern cut into the pliable lamella, the pattern defining a plurality of openings to allow airflow from the vent through the pliable lamella, wherein the plurality of openings account for a majority of an area defined by the outer perimeter of the pliable lamella, the openings of the pliable lamella in fluid communication with the airflow apertures of the vent.

12. The heating, ventilating, and air-conditioning system of claim 11, further comprising a diffuser removably coupled to the vent cover, the diffuser comprising: a cellular material capable of receiving an evaporative liquid.

13. The heating, ventilating, and air-conditioning system of claim 11, wherein the fastener of the pliable lamella comprises a magnet.

14. The heating, ventilating, and air-conditioning system of claim 12, wherein the diffuser comprises a cover coupled to the cellular material and wherein the cover of the diffuser comprises a magnet.

15. The heating, ventilating, and air-conditioning system of claim 12, wherein the diffuser comprises a cover coupled to the cellular material and wherein the cover of the diffuser is configured to camouflage with the pattern of the pliable lamella.

16. The heating, ventilating, and air-conditioning system of claim 12, wherein the diffuser comprises a cover coupled to the cellular material and wherein the cover of the diffuser defines a surface area having a size and geometry that will not pass through the plurality of openings of the vent cover.

17. The heating, ventilating, and air-conditioning system of claim 12, wherein the cellular material of the diffuser holds an essential oil for later evaporation.

18. A method of distributing an airflow, the method comprising:
locating a vent, the vent comprising a plurality of airflow apertures for directing the airflow, the vent having a vent exterior surface transverse to the airflow;
covering the vent with a pliable lamella, the pliable lamella having an exposed side and a vent side, the covering step including the step of facing the vent side toward the vent exterior surface; and
securing the pliable lamella to the vent, the pliable lamella presenting a pattern defining a plurality of openings through the pliable lamella to direct the airflow through the pliable lamella.

19. The method of claim 18, wherein the securing step comprises magnetically adhering the pliable lamella to the vent.

20. The method of claim 18, wherein the securing step comprises adhesively adhering the pliable lamella to the vent.

21. The method of claim 20, wherein the step of adhesively adhering the pliable lamella to the vent comprises the step of adhering a double-sided adhesive strip to the pliable lamella and to the vent.

22. The method of claim 18, further comprising the step of sizing the pliable lamella to cover the vent, the pliable lamella having a stock outer perimeter, the sizing step comprising cutting the pliable lamella to a use outer perimeter different from the stock outer perimeter, the use outer perimeter sized to complement the vent.

23. The method of claim 18, further comprising the step of coupling a diffuser to the vent.

24. The method of claim 23, wherein the step of coupling the diffuser to the vent comprises the step of capturing a diffuser between the vent and the pliable lamella.

25. The method of claim 23, wherein the step of coupling the diffuser to the vent comprises the step of magnetically adhering a cover of the diffuser to the vent.

26. The method of claim 23, wherein the diffuser comprises a cellular material capable of receiving an evaporative liquid; and a cover covering the cellular material.

27. The method of claim 26, wherein the method further comprises the step of charging the cellular material of the diffuser with an essential oil.

28. The method of claim 27, wherein the method of charging the cellular material with the essential oil includes the step of moving the pliable lamella to release the diffuser from a captured position between the vent and the pliable lamella.

29. The method of claim 18, wherein the step of covering the vent comprises forming the pliable lamella from a storage shape non-complementary to the vent to a shape complementary to the vent.

30. The method of claim 29, wherein the step of forming the pliable lamella from a storage shape comprises unrolling the pliable lamella.

31. The vent cover of claim 1, wherein the pliable lamella comprises a magnetized pliable lamella having the pattern cut into the magnetized pliable lamella, the pattern defining the plurality of openings, whereby the fastener comprises a magnetized first side of the pliable lamella.

32. The vent cover of claim 31, wherein the pliable lamella comprises an isotropic magnet sheet.

33. The heating, ventilating, and air-conditioning system of claim 11, wherein the pliable lamella comprises a magnetized pliable lamella having the pattern cut into the magnetized pliable lamella, the pattern defining the plurality of openings, whereby the fastener comprises a magnetized first side of the pliable lamella.

34. The heating, ventilating, and air-conditioning system of claim 33, wherein the pliable lamella comprises an isotropic magnet sheet.

35. The method of claim 18, wherein the pliable lamella comprises a magnetized pliable lamella having a pattern cut into the magnetized pliable lamella, the pattern defining the plurality of openings, whereby the fastener comprises a magnetized first side of the pliable lamella and the step of securing comprises magnetically adhering the magnetized first side of the pliable lamella to the vent.

36. The method 35, wherein the pliable lamella comprises an isotropic magnet sheet.

\* \* \* \* \*